United States Patent [19]

Schutyser et al.

[11] Patent Number: 4,882,226

[45] Date of Patent: Nov. 21, 1989

[54] CARRIER MATERIAL FOR USE IN CHROMATOGRAPHY OR CARRYING OUT ENZYMATIC REACTIONS

[75] Inventors: Jan A. J. Schutyser, Dieren; Antonius J. W. Buser, Wehl, both of Netherlands

[73] Assignee: Akzo N.V., Arnhem, Netherlands

[21] Appl. No.: 94,742

[22] Filed: Sep. 9, 1987

[30] Foreign Application Priority Data

Sep. 23, 1986 [NL] Netherlands .................. 8602395

[51] Int. Cl.$^4$ .................. C12N 11/08; G01N 33/545; C08F 110/00; B32B 5/16
[52] U.S. Cl. .................. 428/407; 210/198.2; 210/656; 428/402; 428/403; 435/180; 436/531; 521/142; 530/810; 530/815
[58] Field of Search .................. 428/402, 403, 407; 210/656, 198.2; 435/180, 181; 436/531, 532; 427/212, 214; 530/810, 815

[56] References Cited

U.S. PATENT DOCUMENTS

| | | | |
|---|---|---|---|
| 4,143,203 | 4/1979 | Rigopulos et al. | 428/407 |
| 4,281,233 | 7/1981 | Coupek et al. | 210/198.2 |
| 4,352,884 | 10/1982 | Nakashima et al. | 435/180 |
| 4,415,700 | 11/1983 | Batz et al. | 524/548 |
| 4,418,152 | 11/1983 | Hosaka et al. | 436/511 |
| 4,650,769 | 3/1987 | Kakimi et al. | 436/533 |
| 4,663,163 | 5/1987 | Hou et al. | 424/101 |
| 4,724,207 | 2/1988 | Hou et al. | 435/180 |

FOREIGN PATENT DOCUMENTS 2077297 10/1971 France.

OTHER PUBLICATIONS

Turkova, "Affinity Chromatography", Journal of Chromatography Library–vol. 12, 1978, pp. 1–2.
Gribnau, et al, "Affinity Chromatography", Les Colloques de l'Inserm, Ed., 1979, p. 175.

Primary Examiner—George F. Lesmes
Assistant Examiner—James B. Monroe
Attorney, Agent, or Firm—Oliff & Berridge

[57] ABSTRACT

A carrier material usable as such in chromatographic separations or as a starting material which, upon linkage to it of compounds containing ionic groups, ligands or bio-active materials can be used as ion exchanger, as a clinical selective adsorbent, as a medium in affinity chromatography or in enzymatic reactions and consists of a core material obtained by addition polymerization of monomers of which at least 50 mole % consists of (meth)acrylic acid or an ester forming equivalent thereof and a hydrophilic coating material, which is covalently bonded to the core by complete or partial conversion of the carboxyl function with a compound containing at least three carbon atoms and an epoxy group, the epoxy groups that are still present having been converted by etherification and/or hydrolysis to form an ester of a compound containing a hydroxyl group or an oligomer thereof having a molecular weight not higher than 1000, as well as a process for preparing the same.

10 Claims, No Drawings

CARRIER MATERIAL FOR USE IN CHROMATOGRAPHY OR CARRYING OUT ENZYMATIC REACTIONS

The invention relates to carrier material usable as such in chromatographic separations or as a starting material which, upon linkage to it of compounds containing ionic groups, ligands or bio-active materials can be used as ion exchanger, as a clinical selective adsorbent, as a medium in affinity chromatography or in enzymatic reactions and consists of a core material obtained by addition polymerization or monomers of which at least 50 mole % consists of (meth)acrylic acid or an ester forming equivalent thereof and a hydrophilic coating material, which is covalently bonded to the core as a result of complete or partial conversion of the carboxyl function with a compound containing at least three carbon atoms and an epoxy group, and to a process for the preparation of such a carrier material. Carrier material of the type indicated above is disclosed in French patent specification No. 2,077,297.

As suitable core material said patent specification mentions, besides a polymer obtained from acrylic acid or derivatives thereof by addition polymerization, in particular polysaccharides, cellulose, polyvinyl alcohol or derivatives thereof.

The covalent bond between the hydroxyl groups-containing core material and the epoxy groups-containing sheath material is effected for instance by reaction with epichlorohydrin in an alkaline medium so than an ether bond is formed. In the case of the carboxyl groups-containing core material, however, use need be made of bisepoxides, as a result of which an ester bond is formed. On the hydrophilic sheath material thus obtained the bio-active materials are subsequently immobilized by direct reaction with the epoxy groups. This reaction not only proceeds slowly, but also has the disadvantage that as a result of the high pH the bio-active materials are partially denatured.

In U.S. Pat. No. 4,143,203 it is therefore proposed that at least 10% of all the carboxyl and carboxylate groups present on the hydrophilic sheath material are esterified to N-hydroxy-succinimide groups, after which the bio-active material can be introduced by substitution. In U.S. Pat. No. 4,352,884 it is proposed that the bio-active materials be directly coupled to the carboxyl groups in the presence of a carbodiimide such as dicyclohexyl-carbodiimide (DCC), 1-ethyl-3-(3-dimethylamino propyl) carbodiimide hydrochloride (EDC) and the like.

Although these well-known carrier materials are suitable for immobilizing bio-active materials such as enzymes, there is particularly for therapeutic purposes a great need for carrier materials which are still more bio-compatible than the well-known materials and which even upon contact with blood do not give rise to coagulation symptoms.

The present invention provides a new type of carrier material on which bio-active materials can be immobilized to such an extent that the loss of activity is even lower than that of the well-known carrier materials and which moreover displays improved chemical and physical stability. The invention consists in that of the carrier material of the type indicated above as known the epoxy groups that are still present have been converted by etherification and/or hydrolysis to form an ester of an hydroxyl group-containing compound or an oligomer thereof having a molecular weight not higher than 1000.

As in the case of the material according to the invention the coating material is covalently bonded to the core material, there is no chance of parts of the coating becoming disassociated and causing complications for instance in the therapeutic field of application.

Owing to the specific preparation of the carrier material according to the present invention, in which the core material is reacted in situ with monomer of the coating material to be formed, the coating material is covalently bonded to the core material and the shape and hence the surface area of the core material can largely be retained. Consequently, a large specific surface area of the core material will result in a large specific surface area of the carrier material. A large specific surface area in combination with proper bio-compatibility and high mechanical stability are prerequisites for a successful use of the carrier material in extracorporeal blood treatment.

Further advantages to the carrier material according to the present invention are that the material does not dissolve in aqueous solutions and does not give rise to non-specific interactions with biomacromolecules. Further, it is resistant to decomposition by microbes and enzymes and it can be sterilized.

The form to be chosen for the carrier material according to the invention will very much depend on the use envisaged. The carrier material may be employed for instance in the form of a tube, pipe, rod, plate, film, porous or non-porous granules or beads or hollow or solid filaments. The form of the substrate or core material will generally be determinative of the form of the carrier material, which form in its turn is governed by the field of application envisaged. For diagnostic uses it will generally be preferred to employ the material in the form of a microtiter plate or a latex dispersion, whereas in therapeutic or chromatographic fields of application preference will be given to carrier material in the form of granules or beads. The polymerization of the core material may be carried out in bulk or in suspension by a method known in the art.

As core material may also be used commercially available products. Rohm & Haas, for instance, supply an ion exchanger under the trade mark Amberlite ® IRC 50. It consists of granules of a polymethacrylic acid cross-linked with divinyl benzene. Another suitable core material made available by the same firm is Amberlite ® XAD-7, which substantially consists of granules of polymethyl methacrylate.

If the carrier material is to be in the form of plate or film, it is preferred that use should be made of linear polymethyl methacrylate as core material. If porous or non-porous beads are to be used, then it is preferred that use should be made of a copolymer of methyl methacrylate and a divinyl compound.

According to the invention it is preferred that use should be made of a carrier material of which the core is formed by a polymer obtained by addition polymerization of a composition of which at least 80 mol. % consists of (meth)acrylic acid or an ester forming equivalent thereof.

When the carrier material is used for chromatographic separations or as a medium for affinity chromatography it is for higher mechanical strength preferred that the polymer of the core should be cross-linked and be present in the form of porous beads having a granulate size in the range of 5 μm to 5 mm.

As cross-linking agent may advantageously be used a divinyl compound such as divinyl benzene, methylene bisacrylamide or ethylene oxide glycol dimethacrylate.

Prior to reaction of the surface of the core material with an epoxy group-containing compound having at least three carbon atoms the carboxyl function, in so far it is still in the form of an ester, must first be saponified with, for instance, a sodium hydroxide solution. Acidification will result in the formation of carboxyl groups which are readily converted with one or more compounds containing an epoxy group.

Carrier material having satisfactory properties is also obtained when the carboxyl function has entirely or in part been converted with epichlorohydrin and subsequently, upon treatment with a sodium hydroxide solution, into an epoxy groups-containing polymer which in its turn can be converted with a biologically active compound after hydrolysis and optional oxidation with periodic acid.

Particularly if the carrier material may come into contact with a readily deactivatable biologically active material it is preferred according to the invention that use should be made of carrier material of which the carboxyl function has entirely or in part been converted with a polyfunctional compound such as butadiene bisepoxide. Use of a polyfunctional epoxy compound results in the carboxyl groups at the surface of the core material being cross-linked to form a strong hydrophilic network.

According to the invention preference is given to carrier material of which the carboxyl function at the surface of the core material has entirely or in part been converted with glycidol.

It should be added that the use of glycidyl acrylate or glycidyl methacrylate as monomer in the preparation of hydrophilic latex particles as carrier material onto which a biologically active material is covalently bonded directly or via a spacer is known from European patent specification No. 54,685. Unlike the carrier material according to the present invention the glycidol in the well-known carrier material is bonded to the carboxyl function of the (meth)acrylic acid via the hydroxyl function of the glycidol, so that the well-known material the epoxy function is still intact prior to conversion with a biologically active material. Moreover, in the case of the well-known material the glycidyl group is present in the core material, which impairs the stability of the carrier material.

According to the invention it is also of advantage to employ carrier material in the preparation of which use is made of glycidyl ethers of polyhydroxy compounds having a molecular weight not higher than 1000.

Particularly favourable results are obtained with polyhydroxy compounds such as glycerol, trimethylol ethane, trimethylol propane, ethylene glycol, propylene glycol, 1,4-butanediol, di- or triethylene glycol, polypropylene oxide glycol or a mono- or polysaccharide.

In this connection it should be added that the use of the glycidyl ether of a mono- or polysaccharide carrier material results in obtaining carrier material whose structure closely resembles that of carrier materials according to U.S. Pat. No. 4,281,233 etherified with a mono- or polysaccharide. The material of the present invention, however, is far more hydrophilic than the well-known carrier material, which is not only due to the hydroxyl group being released upon esterification with glycidol, but is also to be attributed to the fact that by the glycidol route per unit area far more saccharide groups are coupled to the carrier material.

Other glycidyl ethers which may with advantage be used within the scope of the invention are the p-methoxyphenyl glycidyl ether and the p-nitrophenyl glycidyl ether. A very satisfactory carrier material is also obtained, if the vicinal OH groups obtained by reacting the carboxyl function with glycidol have been oxidized into aldehyde groups, which groups can be converted in a known manner with a biologically active compound. As regards the ratio of the amount of hydrophilic coating material to the core material it should be noted that generally carrier material having very good properties is obtained if at least 10% of the carboxyl functions (carboxyl groups or ester forming equivalents thereof) is converted at the surface of the core material to form an ester of a compound containing a hydroxyl group or an oligomer thereof.

Of the core material according to the invention at least 50% consists of polymer obtained preferably by suspension polymerization of (meth)acrylic acid or an ester forming equivalent thereof. Moreover, this polymer may still contain other vinyl monomers with or without reactive group, such as ethylene, propylene, vinyl chloride and/or vinyl acetate.

A prerequisite is that the monomers can be readily polymerized into an addition polymer having the properties required for the use envisaged. For instance, if the material is to be used as cation exchanger, copolymerization may be considered in which use is made of a vinyl monomer having an anionic group. Besides acrylic acid and methacrylic acid, examples of compounds containing an anionic group are vinyl monomers having a sulphonic acid group, such as ethylene sulphonic acid, allyl sulphonic acid, styrene sulphonic acid, 2-sulphoethyl methacrylate, 2-acrylamido-2-methylpropyl sulphonic acid, 3-methacryloyloxy-2-hydroxy-propyl sulphonic acid, the (meth)-acryloyl ester of -hydroxyalkylene sulphonic acid having 1 to 20 carbon atoms in the alkylene group, N-acryloyl taurine, vinyloxybenzene sulphonic acid.

Examples of vinyl monomers having a cationic group are: alkenyl pyridines of the formula:

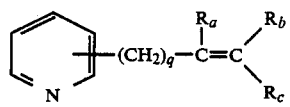

wherein
the alkenyl substituent is in the ortho, meta or para position;
$q=0$ or an integer from 1 to 20 and $R_a$, $R_b$ and $R_c$ may be the same or different and represent a hydrogen atom or an alkyl group having 1 to 20 carbon atoms; amino alkyl acrylates and methacrylates such as t-butylamino ethyl methacrylate, diethylamino ethyl acrylate, dimethylamino propyl methacrylamide and methacrylamido propyl trimethyl ammonium chloride.

For use in affinity chromatography preference is given to a polymer of which at the surface of the core material the carboxyl function has entirely or in part been converted with a compound containing an epoxy group and at least three carbon atoms and the remaining epoxy groups have been converted by etherification and/or hydrolysis with formation of an ester of a compound containing a hydroxyl group or an oligomer thereof having a molecular weight not higher than 1000, as a result of which the material is suitable as such or can be readily coupled to compounds which on the one hand have a reactive group and on the other a ligand suitable for use in a particular field of affinity chromatography.

Very favorable results may be obtained with carrier material of which the hydrophilic coating material is linked, optionally via a spacer group, to one or more of the following groups:

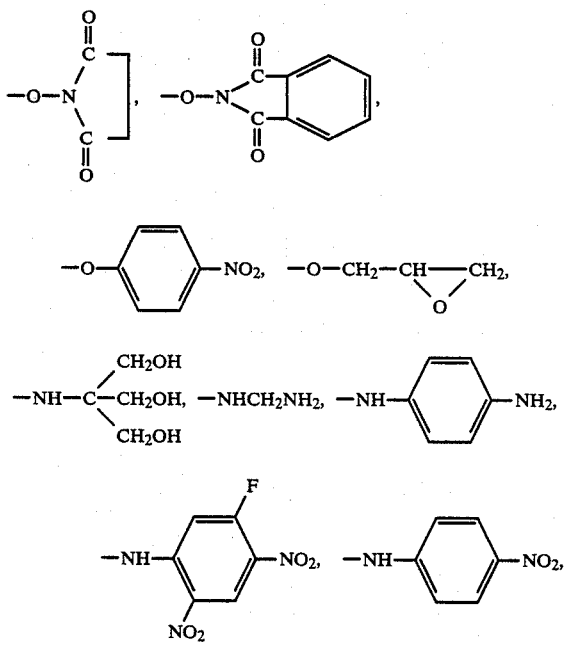

In the preparation of the starting material use may still also have been made of vinyl monomers in which the envisaged groups suitable for use in affinity chromatography are already present or of vinyl monomers having reactive groups that can be readily coupled to compounds which on the one hand have a reactive group and on the other a ligand suitable for use in a particular field of affinity chromatography.

To affinity chromatography the same meaning is attributed here as done by Turkova in "Affinity Chromatography", Elsevier, 1978, pp. 1 and 2. So not only affinity methods in the sense of bio-specific adsorption are covered by it, but also hydrophobic chromatography, covalent chromatography, affinity elution as well as the study of interactions on support materials to which oligonucleotides are bonded. By affinity chromatography is also to be understood the isolation of biomacromolecules by simple sorption on a specific sorbent.

In addition to the aforementioned vinyl monomers having an anionic or cationic group examples of vinyl monomers having reactive groups include: halogenated monomers, such as halogenated alkyl acrylates or methacrylates. As examples thereof may be mentioned: 2-chloroethyl acrylate and 2-chloroethyl methacrylate; halogenated alkyl acrylic acid and compounds derived therefrom having the formula:

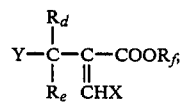

wherein $R_d$ and $R_e$ may be the same or different and represent a hydrogen atom, a methyl group or an ethyl group and $R_f$ represents a hydrogen atom, a lower alkyl group or an aryl group, X stands for a hydrogen atom, halogen, CN, an aryl group, OH, COOH, or O-aryl and Y represents a chlorine or bromine atom; and halomethylated styrene such as p-chloromethyl styrene.

Further examples include: reactive heterocyclic vinyl monomers such as 2-(1-aziridinyl)ethyl methacrylate, allyl glycidyl ether, glycidyl methacrylate, thioglycidyl acrylate, N-vinyl-2-pyrrolidone and maleic anhydride; vinyl monomers having an aldehyde end group, such as acrolein and crotonaldehyde; vinyl monomers having an amino group, such as allyl amine, vinyl amine and p-amino styrene; acid monomers such as maleic acid, fumaric acid, itaconic acid and acids of the formula:

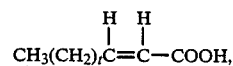

wherein t=0 or an integer from 1 to 20: compounds derived from acrylic acid, such as $Cl_2C=CH\ COOH$; vinyl alkylene carboxylic acid having 2 to 20 carbon atoms in the alkylene group; p-vinyl benzoic acid; alkyl vinyl ether having 1 to 18 carbon atoms in the alkyl group; vinyl phenyl ether; hydroxyalkylene vinyl ether having 2 to 20 carbon atoms in the alkylene group; the vinyl ether of a polyalkylene oxide glycol having 2 to 20 alkylene oxide units and 2 to 5 carbon atoms per alkylene oxide unit; compounds of the formula:

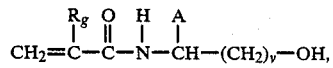

wherein $R_g$ has the meaning of a hydrogen atom or an alkyl group having 1 to 18 carbon atoms, and A represents a hydrogen atom or an alkyl group having 1 to 20 carbon atoms and v represents an integer from 1 to 20.

According to the invention it is of advantage if the molecular weight of the vinyl monomer having a functional group and possibly also a spacer group is not more than 1000 and preferably in the range of 70 to 400.

Examples of ligands suitable for use in affinity chromatography include amino acids, mononucleotides, oligonucleotides and polynucleotides, various organic colourants, enzyme inhibitors, polyamino acids, lectins, polysaccharides, lipids, antigens, enzymes.

The invention also relates to a process for the preparation of carrier material of the well-known type mentioned in the opening paragraph, in which
(A) in a manner known in chemical technology a (co)-polymer is prepared from a monomer composition of which at least 50 mole % consists of (meth)acrylic acid or an ester forming equivalent thereof,
(B) the resulting (co)polymer is converted with a compound containing at least three carbon atoms and an epoxy group in an organic, polar solvent and in the presence or not of a basic or acid catalyst, after which the epoxy groups that may still be present or converted by etherification and/or hydrolysis to form an ester of a compound containing a hydroxyl group or an oligomer thereof having a molecular weight not higher than 1000, and (C) the material in the presence of vicinal hydroxyl groups is optionally further oxidized with periodic acid with formation of one aldehyde group per two vicinal hydroxyl groups or the material is converted with compounds having reactive groups in a manner known in chemical technology.

The invention will be further described in the following examples. It will be clear that these examples merely serve to illustrate the present invention and that they constitute no limitation on the scope thereof.

EXAMPLE I 150 g of beads of polymethacrylic acid cross-linked with divinyl benzene (Amberlite ® IRC-50; bead size 0.3 to 0.84 mm; average pore diameter 150 nm; 10 meq of carboxylic acid groups per gram of dry material) were thoroughly washed with distilled water, dilute hydrochloric acid (5%), distilled water and water-free dioxane until all ions and low molecular weight compounds were removed.

The beads were transferred to a 2-liter three-necked flask fitted with a stirrer, a reflux condenser and a $CaCl_2$ tube, after which 300 ml of water-free dioxane were added. Subsequently, 111 g of glycidol (1.5 moles) and as a catalyst 1.1 g of tetramethyl ammonium chloride and 450 ml of water-free dioxane were added. Thereupon the suspension was heated on an oil bath for 4 hours, with refluxing and stirring. After cooling and standing overnight the beads were thoroughly washed with 3l of dioxane, 5l of distilled water, 500 ml of 3N NaOH and 500 ml of a 2M NaCl solution in water. Finally, the beads were introduced into a mixture of 250 ml of dioxane and 250 ml of a 2M NaCl solution in water. After standing overnight the suspension was treated with distilled water until the suspension and the filtrate reacted neutral.

The amount of glycidol not bound to the beads were determined gravimetrically be weighing the total amount of residue after evaporating the dioxane from the reaction liquid (devoid of beads) and the first washing liquid and deducting from it the amount of catalyst.

By deducting from the amount of glycidol applied for the modification the amount of unreacted glycidol it can be calculated that 8.2 mmoles of glycidol or 606.8 mg of glycidol per g of dry starting resin were incorporated.

Subsequently of another fraction the amount of vicinal hydroxyl groups present were oxidized with periodic acid. The resulting formaldehyde was reacted with acetyl acetone and ammonia to form diacetyl dihydrolutidin and the concentration thereof was measured spectophotometrically at 410 nm. By this method of determination it was found that per g of dry starting material 8.1 mmoles of vicinal diol groups were incorporated.

Use of 10 mmoles of glydicol per g of starting resin consequently resulted in incorporation of 8.3 mmoles, of which 8.1 mmoles with vicinal OH groups. So the degree of oligomer formation by etherification is very low here.

EXAMPLE II

Use being made of the same procedure as described in Example I, beads of polymethacrylic acid cross-linked with divinyl benzene were brought into reaction with 5 mmoles of glycidol per g of Amberlite ® IRC-50. Both spectophotometrically and gravimetrically it was found that per g of dry Amberlite ® 4.5 mmoles of glycidol were incorporated. By microtitration the amount of non-converted carboxyl groups were found to be 3 mmoles/g. p The resulting reaction product was suitable for use as weakly acid ion exchanger in the purification of proteins.

EXAMPLE III

Use being made of the same procedure as described in Example I, Amberlite ® IRC-50 beads were brought into reaction with glycidol, but in this case use was made of 30 mmoles of glycidol per g of Amberlite ® IRC-50.

Spectrophotometrically, it was found that per g of dry, novel carrier 5.6 mmoles of vicinal diol groups were incorporated. Gravimetrically, it was found that per g of dry Amberlite ® IRC-50 20 mmoles of glycidol were converted or 8.1 mmoles of glycidol per g of dry, novel carrier.

From the difference between the gravimetrically and the spectrophotometrically found values it follows that a substantial part of the glycidol was incorporated with formation of an oligoether structure with terminal vicinal hydroxyl groups.

EXAMPLE IV

Use being made of the same procedure as described in Example I, Amberlite ® IRC-50 (AM-50) beads were brought into reaction with 1,3-diglycidyl glycerol (digl-GL) and/or glycidol (gl.) used in the amounts given in the table below. All the reactions were carried out in the presence of 1% by weight of tetramethyl ammonium chloride, calculated on the amount of epoxy compound(s) used.

Sample E was prepared by first reacting Amberlite ® IRC-50 exclusively with the bisepoxide for 4 hours and subsequently adding glycidol, after which the resulting mixture was allowed to react for 1 more hour.

Sample F was prepared by first reacting Amberlite ® IRC-50 for 30 minutes with the diglycidyl ether of polypropylene oxide glycol having a molecular weight of about 640 (digl-PPO) and subsequently, after adding glycidol, allowing the suspension to react for 3 hours.

TABLE 1

| Sample | mmoles epoxide or g epoxide per g dry Am-50 | mmoles and/or g epoxide incorporated per | | vicinal diol groups (mmoles) per modified carrier |
|---|---|---|---|---|
| | | g dry Am-50 | g dry modified carrier | |
| A | 1.48 g (7.3 mmoles) digl-GL | 0.77 (3.8 mmoles) | 0.44 (2.1 mmoles) | 0.4 |
| B | 2.38 g (11.7 mmoles) digl-GL | 0.89 (4.4 mmoles) | 0.47 (2.3 mmoles) | 0.8 |
| C | mixture of 0.7 mmoles digl-GL and | 0.48 | 0.32 | 3.1 |

TABLE 1-continued

| Sample | mmoles epoxide or g epoxide per g dry Am-50 | mmoles and/or g epoxide incorporated per | | vicinal diol groups (mmoles) per modified carrier |
|---|---|---|---|---|
| | | g dry Am-50 | g dry modified carrier | |
| D | 8 mmoles gl (in all 0.73 g) mixture of 2.2 mmoles digl-GL and 5.9 mmoles gl (in all 0.88 g) | 0.46 | 0.32 | 2.8 |
| E | 3.7 mmoles digl-GL and 4 hours later 10 mmoles gl (in all 1.5 g) | 0.99 | 0.50 | 4.0 |
| F | 0.5 mmoles digl-PPO and later 10 mmoles gl (in all 1.060 g) | 0.37 | 0.27 | |

The small proportion of vicinal diol groups in the samples A and B relative to the proportion of digl-GL incorporated per g of the new carrier must be attributed to hydrolysis of epoxy groups present in the new carrier.

EXAMPLE V 50 g of polymethyl methacrylate beads 1.1 to 2.2 mm in diameter (average pore size 106 nm, volume 0.78 ml/g, specific surface area 26 $m^2$/g of dry beads) were introduced into a 1-1 l three-necked flask. The three-necked flask was fitted with a reflux condenser and a stirrer. To the contents of the three-necked flask there were successively added 200 g of isopropyl alcohol and, with stirring, 50 g of sodium hydroxide in 50 ml of water and again 200 g of isopropyl alcohol. After boiling under reflux for 48 hours and cooling to room temperature the beads were filtered, washed with 3 l of isopropyl alcohol, 1 l of 50/50 mixture of ethanol and water and distilled water until the filtrate reacted neutral. Subsequently, the beads were successively treated with 5%-hydrochloric acid, distilled water, 5%-ethanol in water, water, methanol and dioxane. By microtitration it was found that 1 g of dry hydrolysed beads contained 2.2 meq of carboxylic acid groups.

Use being made of the same procedure as given in Example I, 24 g of wet beads (corresponding to 10 g of dry polymer) were brought into reaction with 7.4 g (=mmoles of glycidol) in the presence of 74 mg of tetramethyl ammonium chloride and 50 ml of water-free dioxane. After a reaction time of 4 hours the beads were treated in the same way as indicated in Example I. Spectrophotometrically it was found that per g of modified carrier 2.6 mmoles of vicinal diol groups were present.

EXAMPLE VI

To 30 ml of wet beads of Example I treated with glycidol (corresponding to 10 g of dry beads) were added 180 ml of 0.0675 M sodium periodate. After 2 hours stirring at room temperature part of the vicinal diol groups were oxidized to aldehyde groups. Subsequently, the beads were thoroughly washed successively with distilled water and an 0.1M phosphate buffer at pH=8.62. After the beads had been transferred to a flask, the buffer liquid above the level of the settled beads were removed, after which to the wet beads 14 mg of an L-Asparaginase-containing preparation (10,000 I.U. per flask) in 25 ml of 0.1M phosphate buffer (pH=8.2) were added. After 1 hour's stirring under nitrogen at room temperature the sample was washed on a glass filter successively with 0.1M Tris-HCl-buffer (pH=8.5) containing 0.5M NaCl and 0.1M phosphate buffer (pH=7.4).

A sample of the immobilized enzyme preparation thus obtained was incubated at 37° C. with stirring, in a 33 mM solution of L-asparagine (in 0.1 M phosphate buffer at pH=7.4). The conversion of L-asparagine into L-asparaginic acid was determined by HPLC. It was found that per g of dry immobilized preparation 135 $\mu$ moles of substrate per minute had been converted, i.e. per gramme 135 units had been bonded. Upon repetition of the experiment on beads not oxidized with periodate no enzyme activity was found to be built in, which means that L-Asparaginase was not adsorbed on the hydrophilic carrier material.

EXAMPLE VII

Use being made of the same procedure was described in Example VI, the vicinal OH groups of the beads treated in accordance with the Examples II, III and IV D and of beads obtained by reacting 15 mmoles of glycidol per gramme of Amberlite ® IRC-50 were oxidized with periodic acid with formation of aldehyde groups. The resulting samples A (of Example II), B (of product obtained upon reaction of 15 mmoles of glycidol per g of Amberlite ®), C (of Example III). D (of Example IV D) and E (of Example V) were loaded with L-Asparaginase.

The data in Table 2 show that the activity found on the beads relative to that which had disappeared from the coupling solution is high.

TABLE 2

| Sample | Examples of preparing a carrier converted with periodic acid | units per g of dry carrier | | | HPLC-determined proportion of protein bound per g of dry carrier |
|---|---|---|---|---|---|
| | | prior to coupling reaction | found in coupling buffer after coupling | coupled | |
| A | Example II | 170 | 136 | 50 | 0.2 |
| B | Example I, but by reaction of 15 mmoles of glycidol with 1 g of Amberlite IRC-50 | 316 | 63 | 124 | 0.9 |
| C | Example III | 319 | 267 | 34 | 0.07 |

TABLE 2-continued

| Sample | Examples of preparing a carrier converted with periodic acid | units per g of dry carrier | | | HPLC-determined proportion of protein bound per g of dry carrier |
|---|---|---|---|---|---|
| | | prior to coupling reaction | found in coupling buffer after coupling | coupled | |
| D | Example IV D | 232 | 151 | 75 | — |
| E | Example V | 116 | 94 | 33 | 0.2 |

EXAMPLE VIII

Use being made of the procedure described in Example VI, 30 ml of wet beads prepared in accordance with Example I were oxidized with sodium periodate. Subsequently, 25 ml of a solution of 34 mg of L-Arginase (about 20 units per mg) were added. After 1 hour's stirring under nitrogen at room temperature the beads were washed with 30.1M Tris-HCL buffer (pH=8.5 and consisting of an 0.5M NaCl solution and an 0.1M phosphate buffer of pH=7.4).

A sample of the L-Arginase-containing beads thus obtained was incubated in a solution of 37° C. of 0.1M L-arginine in an 0.1M phosphate buffer (pH=7.4) which also contained 2 mM $MnCl_2$. The progress of the conversion of L-arginine into ornithine and urea was followed by means of HPLC. It was found that per g of dry carrier 44 units of the enzyme preparation were immobilized. After filtration of the beads the absence of any conversion in the filtrate showed that it contained no free enzyme.

The same activity (44 units per g of dry carrier) was observed after incubation of the beads in blood serum to which L-arginine (33 mM) had been added.

When under the above conditions L-Arginase was brought into contact with the beads not oxidized with periodate, there was found to have been no adsorption of L-Arginase on the carrier.

EXAMPLE IX 60 ml of filter-dry beads wetted with water ($\approx$20 g of dry beads) prepared by the process described in Example I were treated with 4 g of a reactive azo dye in conformity with a method of Gribnau et al. on page 175 in Affinity Chromatography, Les Colloques de l'Inserm, Ed. by J. M. Egly, Paris (1979). Use was made of an azo dye supplied by Bayer under the trade mark Brilliant Red E-4BA ®. During stirring the suspension was set to pH=8 with 2M NaOH and after 1 night's stirring at room temperature it was thoroughly washed with water.

After the red coloured beads had been sucked dry, they were reduced for 30 minutes at 60° C. with a solution of 10 g of sodium dithionite in 150 ml of water. The beads thus decoloured were successively washed with water, 2N NaOH, 2M NaCl and water until the washing liquid reacted neutral. 7.5 ml of the beads thus treated were suspended in 3N HCL solution at about 0° C. To the stirred suspension there were added portionwise and at a temperature of <5° C. 18 ml of cold 1M sodium nitrite solution. Fifteen minutes after all of the nitrite had been added, the beads were washed on a glass filter with ice-cold water and a borate buffer of pH=8.5. To the beads thus loaded with diazonium groups were added a cold solution of a 3.4 mg L-Asparaginase-containing enzyme preparation in 5 ml of 0.1M borate buffer (pH=8.5). After the beads had been stirred overnight under a nitrogen atmosphere, they were washed with an 0.1M Tris-HCl buffer (0.5M NaCl, pH=8.5) and 0.1M phosphate buffer (pH=7.4).

Per gramme of dry beads about 0.5 mg of protein and 50 activity units of the L-Asparaginase were bonded. After washing with water the bio-active beads were freeze-dried at 0° C. and stored for 1 month at 4° C. They were found to have retained 80% of their original activity.

L-Arginase was bonded to 7.5 ml of diazotized beads. After incubation for 1 night at 5° C. with a solution of 13 mg of enzyme in 5 ml of 0.1M borate buffer and 10 mM $MnCl_2$ at pH=8.5 the sample was treated in the same way as indicated hereinbefore for L-Asparaginase. An activity of 30 units per gramme of dry material was observed. After freeze-drying this activity was found to have decreased to 24 units per gramme.

EXAMPLE X

Use being made of the same procedure as described in Example I, Amberlite ® IRC-50 beads 0.08 to 0.1 mm in diameter were modified with glycidol. The concentration was 15 mmoles of glycidol per gramme of beads. After termination of the reaction it was found gravimetrically that per gramme of dry starting material 9.6 mmoles of glycidol had been built in.

30 ml of these beads (corresponding to 10 g of dry carrier material) were treated with 180 ml of 0.0675M sodium periodate in the same was as described in Example VI.

After washing with water and a buffer A consisting of 0.1M sodium acetate (pH=6.5) with 1 mM $MnCl_2$, 1 mM $MgCl_2$ and 1 mM $CaCl_2$ the beads loaded with aldehyde groups were transferred to a flask, and the liquid above the beads was removed by suction and a solution of 100 mg of Conconavaline A (Con A) in 60 ml of a buffer liquid B was added to the beads. The buffer liquid contained 0.1M NaOAc (pH=5) with 1 mM $MnCl_2$, 1 mM $CaCl_2$, 1 mM $CaCl_2$, 1M NaCl and 0.2M α-methyl-D-mannoside. After adjusting the pH to 5 with 4N acetic acid, the suspension was stirred under nitrogen at room temperature with the aid of a rotating vacuum evaporator. After 2 hours the beads were successively washed with buffer liquid B, buffer liquid A, buffer liquid A containing an additional amount of 1M NaCl and finally again with buffer liquid A. By size exclusion HPLC it was found that during the immobilization reaction about 2 mg of Con A per gramme of dry, novel carrier (or 0.7 mg/ml of wet carrier) had been removed by the beads from buffer A.

Into a column having an internal diameter of 1 cm were introduced 15 ml of wet beads treated with Con A. The column was successively equilibrated with buffer A and charged with 80 ml of a solution of 0.25 mg of Horse radish peroxidase per ml of buffer A at a flow rate of 20 ml per hour. The solution passed through the column was collected in successive 20 ml fractions. By extinction measurements both at 280 and 405 nm the peroxide contents in the starting solution and the fractions were determined. It was found that per ml of adsorbent 0.15 mg of peroxidase was bound. After the column had been flushed with buffer A, the adsorbed peroxidase was completely removed from the column by elution with buffer A to which 1M NaCl and 1M α-methyl mannoside had been added. Before the column was again loaded with peroxidase solution, it was first equilibrated successively with buffer A, with an additional amount of 1M NaCl and buffer A. After loading it was found that the amount of peroxidase bound was the same as on the first occasion.

EXAMPLE XI

To 10 g of beads of Example I contained in a three-necked flask equipped with a stirrer, a reflux condenser, a CaCl$_2$ tube and a thermometer there were successively added 45 ml of waterfree dioxane, 3.6 g of 1,3-diglycidyl glycerol and 4.5 g of diethyl amino ethanol. After 1 day's heating with stirring under reflux the reaction mixture was cooled and washed on a glass filter successively with 200 ml of dioxane, 200 ml of water, 200 ml of 4N HCl, 300 ml of 2M NaCl and water until neutral. By microtitration 2 meq of ionic groups per gram of dry material were found on the diethylaminoethanol (DE AE) ion exchanger.

The ion exchanger was equilibrated with 0.01M Tris at pH=8.0 and subsequently incorporated in 36 ml of 0.01M Tris buffer (pH=8.0) per gram of ion exchanger.

The suspension was stirred for 6 hours by means of a rotating vacuum evaporator. By determining the residual protein content in the liquid above the beads by means of HPLC the progress was followed of the removal of the albumin from the solution by the ion exchanger. After one hour's adsorption the ion exchanger was found to have its maximum capacity of 9.3 mg/gram of (dry) resin. After the column had been packed with the ion exchanger loaded with albumin, the adsorbent was first afterwashed with the adsorption buffer and subsequently eluated with 0.01M Tris buffer (pH=8.0) containing 1.0M NaCl. All the albumin adsorbed (9.3 mg/g resin) was recovered in the elution fractions. After equilibration of the column the ion exchanger could again be loaded with albumin in entirely the same manner and be eluated to obtain identical results. When the same experiment was applied to a non-modified carrier no adsorption or desorption of albumin could be observed.

EXAMPLE XII 36 ml of carrier material prepared in accordance with Example I were washed with a mixture of equal parts by weight of dioxane and water and subsequently with dry dioxane. After the beads had been sucked dry on a glass filter, 4.45 g (24 mmoles) of p-nitrobenzoic chloride in 75 ml of dry dioxane were added. After 30 minutes' boiling with refluxing 2.5 ml of waterfree pyridine were added. After another 30 minutes boiling with refluxing and cooling the sample was treated with dioxane and water. The covalently bonded nitro groups of the carriers were reduced in the same manner as indicated in Example IX and converted into diazonium groups. Coupling of L-Asparaginase in the manner given in Example IX yielded an immobilized preparation with 37 units per g of carrier material. The activity of the carrier material thus loaded was not appreciably impaired by freeze drying at 0° C.

We claim:

1. A carrier material usable as such in chromatographic separations or as a starting material which, upon linkage to it of compounds containing ionic groups, ligands or bio-active materials can be used as an ion exchanger, as a clinical selective adsorbent, as a medium in affinity chromatography or in enzymatic reactions and comprises granules of a core material obtained by addition polymerization of monomers of which at least 50 mole % comprise (meth)acrylic acid or an ester forming equivalent thereof other than an ester of glycidol and a hydrophilic coating material, which is covalently bonded to the core by complete or partial conversion of the carboxyl function with a compound containing at least three carbon atoms and epoxy group into an ester, characterized in that the compound containing at least three carbon atoms and an epoxy group is glycidol or glycidol etherified with a polyhydroxy compound having a molecular weight not higher than 1000 and that esters in which epoxy groups are still present are further reacted by etherification and/or hydrolysis to form a compound containing a hydroxyl group or an oligomer therof having a molecular weight not higher than 1000.

2. A carrier material according to claim 1, characterized in that at least 80 mole % of the monomers from which the core material is built up comprises (meth)acrylic acid or an ester forming equivalent thereof.

3. A process for the preparation of carrier material according to claim 1 in which (A) in a manner known in chemical technology a (co)polymer is prepared from a monomer composition of which at least 50 mole % comprises (meth)acrylic acid or an ester forming equivalent thereof other than an ester of glycidol to form polymeric granules, (B) the resulting (co)polymer is converted with glycidol or glycidol etherified with a polyhydroxy compound having a molecular weight not higher than 1000 in an organic, polar solvent and in the presence or not of a basic or acid catalyst after which the epoxy groups that may still be present are converted by etherification and/or hydrolysis to form an ester of a compound containing a hydroxyl group or an oligomer thereof, and (C) the material in the presence of vicinal hydroxyl groups is optionally further oxidized with periodic acid with formation of one aldehyde group per two vicinal hydroxyl groups or the material is converted with compounds having reactive groups in a manner known in chemical technology.

4. A carrier material according to claim 1, characterized in that the hydrophilic coating material is linked, directly or via a spacer group, to one or more of the following groups:

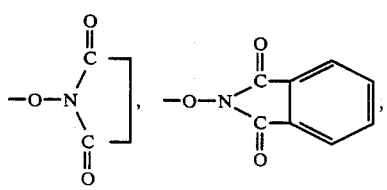

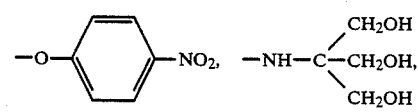

-continued

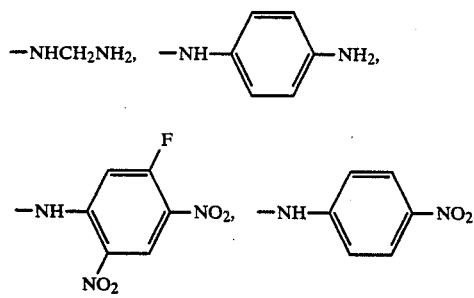

5. A carrier material according to claim 1, characterized in that the vicinal OH groups obtained by conversion with glycidol have been converted into aldehyde groups by oxidation with periodic acid.

6. A carrier material according to claim 1, characterized in that the polymer is cross-linked and is present in the form of porous beads having a granulate size in the range of 5 μm to 5 mm.

7. A carrier material according to claim 1, characterized in that the polyhydroxy compound is selected from the group consisting of glycerol, trimethylol ethane, trimethylol propane, ethylene glycol, propylene glycol, 1,4-butanediol, diethylene glycol, triethylene glycol, polypropylene oxide glycol, a monosaccharide and a polysaccharide.

8. A carrier material according to claim 1, characterized in that at least 10% of the carboxyl functions at the surface of the core material has been converted to form an ester of a compound containing a hydroxyl group or an oligomer thereof.

9. A carrier material according to claim 1, characterized in that the polymer is cross-linked with a divinyl compound.

10. The carrier of claim 9 wherein said divinyl compound is selected from the group consisting of divinyl benzene, methylene bisacrylamide and ethylene glycol dimethacrylate.

* * * * *

UNITED STATES PATENT AND TRADEMARK OFFICE
CERTIFICATE OF CORRECTION

PATENT NO. : 4,882,226

DATED : November 21, 1989

INVENTOR(S) : Jan A.J. SCHUTYSER et al

It is certified that error appears in the above-identified patent and that said Letters Patent is hereby corrected as shown below:

Col. 9, line 46, change "(=mmoles)" to --(=100 mmoles)--.

Col. 10, line 28, change "0.1M Iris-" to --0.1 M Tris---.

Col. 11, line 19, change "30.1M" to --0.1 M--.

Col. 12, line 37, change "was" to --way--;

line 41, change "$CaCl_2$the" to --$CaCl_2$ the--;

line 47, change "$CaCl_2$" (first occurrence only) to --$MgCl_2$--;

IN THE CLAIMS:

Claim 5, col. 15, line 2, delete "the".

Signed and Sealed this

Fifteenth Day of January, 1991

Attest:

HARRY F. MANBECK, JR.

Attesting Officer

Commissioner of Patents and Trademarks